United States Patent
Chung

(10) Patent No.: US 11,213,565 B2
(45) Date of Patent: Jan. 4, 2022

(54) PROTEIN P8 DERIVED FROM LACTIC ACID BACTERIA AND ITS USE AS ANTI-CANCER AGENT

(71) Applicant: CELL BIOTECH CO., LTD., Gyeonggi-do (KR)

(72) Inventor: Myung Jun Chung, Seoul (KR)

(73) Assignee: CELL BIOTECH CO., LTD., Gyeonggi-do (KR)

( * ) Notice: Subject to any disclaimer, the term of this patent is extended or adjusted under 35 U.S.C. 154(b) by 396 days.

(21) Appl. No.: 16/303,208

(22) PCT Filed: Feb. 15, 2017

(86) PCT No.: PCT/KR2017/001625
§ 371 (c)(1),
(2) Date: Nov. 20, 2018

(87) PCT Pub. No.: WO2018/097402
PCT Pub. Date: May 31, 2018

(65) Prior Publication Data
US 2019/0201481 A1 Jul. 4, 2019

(30) Foreign Application Priority Data
Nov. 28, 2016 (KR) .......................... 10-2016-0159479

(51) Int. Cl.
*A61K 38/00* (2006.01)
*A61P 35/00* (2006.01)
*A61K 38/16* (2006.01)
*A61K 35/744* (2015.01)
*A23L 33/18* (2016.01)
*C07K 14/335* (2006.01)
*C12N 15/74* (2006.01)
*A61K 35/00* (2006.01)

(52) U.S. Cl.
CPC ............ *A61K 38/164* (2013.01); *A23L 33/18* (2016.08); *A61K 35/744* (2013.01); *A61K 38/16* (2013.01); *A61P 35/00* (2018.01); *C07K 14/335* (2013.01); *C12N 15/74* (2013.01); *A23V 2002/00* (2013.01); *A61K 2035/115* (2013.01); *Y02A 50/30* (2018.01)

(58) Field of Classification Search
None
See application file for complete search history.

(56) References Cited

U.S. PATENT DOCUMENTS 10,016,468 B2 * 7/2018 El-Nezamy .......... A61K 35/744

FOREIGN PATENT DOCUMENTS

| KR | 10-0232639 B1 | 12/1999 |
| KR | 10-2011-0124516 A | 11/2011 |
| KR | 10-2012-0015644 A | 2/2012 |
| KR | 10-1427363 B1 | 8/2014 |
| KR | 10-2016-0084822 A | 7/2016 |
| KR | 10-1656208 B1 | 9/2016 |

OTHER PUBLICATIONS

Orlando et al. (2016, Int. J. Oncology, vol. 48, pp. 2629-2638) (Year: 2016).*
NCBI Web Printout—2 pages. (Year: 2013).*
Escamilla et al., Cell-Free Supernatants from Probiotic Lactobacillus casei and Lactobacillus rhamnosus GG Decrease Colon Cancer Cell Invasion In Vitro, Nutrition and Cancer, vol. 64, No. 6, Aug. 1, 2012, pp. 871-878, XP055641523.
Extended European Search Report from corresponding European Application No. 17874171.6 dated Nov. 21, 2019.
Khan et al., Gut Microbiota and Probiotics: Current Status and Their Role in Cancer Therapeutics, Drug Development Research, vol. 74, No. 6, Jul. 3, 2013, pp. 365-375, XP055289994.
Kim et al., Cancer chemopreventive effects of lactic acid bacteria, Journal of the All-India Ophthalmological Society, Medknow Publications and Media Pvt. Ltd, India, vol. 17, No. 8, Jan. 1, 2007, pp. 1227-1235, XP008160403.
Uniprot Db, "UPI00019F7D40", Uniprot, Jun. 16, 2009, XP055641481, https://www.uniprot.org/uniparc/UPI00019F7D40.
Zhong et al, Emerging roles of lactic acid bacteria in protection against colorectal cancer, World Journal of Gastroenterology, vol. 20, No. 24, Jan. 1, 2014, pp. 7878-7886, XP055531727.
NCBI GenBank Accession No. WP_005686763.1, (2013).
NCBI GenBank Accession No. EEN79819.1, (2013).
Sadeghi-Aliabadi, H., et al. (2014) "Effects of Lactobacillus plantarum A7 with probiotic potential on colon cancer and normal cells proliferation in comparison with a commercial strain.", *Iran J Basic Med Sci*, 17(10):815-819 (Oct. 2014).
International Search Report from corresponding PCT Application No. PCT/KR2017/001625 dated Nov. 27, 2017, with an English translation.

* cited by examiner

*Primary Examiner* — Thea D'Ambrosio
(74) *Attorney, Agent, or Firm* — Harness, Dickey & Pierce, P.L.C.

(57) ABSTRACT

The present invention relates to a protein derived from lactic acid bacteria and a method for producing the same. The lactic acid bacteria-derived protein of the present invention is a purified protein isolated from lactic acid bacteria (*Lactobacillus rhamnosus*) having an excellent therapeutic effect against colorectal cancer. It has been demonstrated to have a remarkable effect against colorectal diseases, and thus is expected to be widely used as a natural protein therapeutic agent against colorectal diseases in the medical field.

8 Claims, 11 Drawing Sheets
Specification includes a Sequence Listing.

PROTEIN P8 DERIVED FROM LACTIC ACID BACTERIA AND ITS USE AS ANTI-CANCER AGENT

CROSS-REFERENCE TO RELATED APPLICATIONS

This application is a national phase application of PCT Application No. PCT/KR2017/001625, filed on Feb. 15, 2017, which claims the benefit and priority to Korean Patent Application No. 10-2016-0159479, filed Nov. 28, 2016. The entire disclosures of the applications identified in this paragraph are incorporated herein by references.

FIELD

The present invention relates to a protein derived from lactic acid bacteria and a method for producing the same.

BACKGROUND

The term "colorectal diseases" refers to various diseases that occur in the large intestine, including colorectal cancer, colitis, irritable bowel syndrome, Crohn's disease, and the like. In modern times, the number of patients with colorectal diseases has increased greatly due to frequent stress, Westernized eating habits, drinking, and the like. According to a 2012 report by the Korean National Health Insurance Corporation on colorectal cancer treatment costs, the number of colon cancer patients increased from 77,193 in 2007 to 113,504 in 2011, and the cost of colorectal cancer treatment increased from 336 billion Won in 2007 to 514.8 billion Won in 2011. For treatment of colorectal cancer, synthetic compounds have been developed and used, including fluoropyrimidine-based drugs, such as 5-FU (fluorouracil), UFT (tegafur-uracil), capecitabine and the like, as well as irinotecan, oxaliplatin and the like, and targeted agents have been developed, including bevacizumab (trade name Avastin), cetuximab (trade name Erbitux) and the like. However, since these agents have a high risk of side effects due to high-dose administration and long-term use, development of natural therapeutic agents derived from natural products is urgently required.

Meanwhile, the term "probiotics" refers to strains that exert beneficial effects on the intestinal environment when reached the intestines after intake. Most probiotics known to date are lactic acid bacteria, and the term "lactic acid bacteria" refers to bacteria that ferment sugars to obtain energy and produce a large amount of lactic acid. It is known that administration of lactic acid bacteria to patients with colorectal diseases, including colorectal cancer and colitis, can exhibit therapeutic effects. Thus, technologies of using lactic acid bacteria to treat colorectal diseases have been developed (KR 10-0232639 B1, entitled "Novel Korean Lactic Acid Bacteria Inhibiting Activity of Intestinal Harmful Enzyme and Use Thereof", and KR 10-2016-0084822 A, entitled "Nano-Type Kimchi Lactic Acid Bacteria Composition Having Effect of Improving Intestinal Environment"). However, the development of technologies related to the identification of a protein as an active ingredient in lactic acid bacteria and the use thereof is still insufficient.

Therefore, the present invention is directed to a protein derived from lactic acid bacteria and a method for producing the same. The lactic acid bacteria-derived protein of the present invention is a purified protein isolated from lactic acid bacteria (*Lactobacillus rhamnosus*) having an excellent therapeutic effect against colorectal cancer. It has been demonstrated to have a remarkable effect against colorectal diseases, and thus is expected to be widely used as a natural protein therapeutic agent against colorectal diseases in the medical field.

DISCLOSURE

Technical Problem

The present invention has been made in order to solve the above-described problems occurring in the art, and is directed to a protein derived from lactic acid bacteria and a method for producing the same.

However, objects which are to be achieved by the present invention are not limited to the above-mentioned object, and other objects of the present invention will be clearly understood by those skilled in the art from the following description.

Technical Solution

Hereinafter, various embodiments described herein will be described with reference to figures. In the following description, numerous specific details are set forth, such as specific configurations, compositions, and processes, etc., in order to provide a thorough understanding of the present invention. However, certain embodiments may be practiced without one or more of these specific details, or in combination with other known methods and configurations. In other instances, known processes and preparation techniques have not been described in particular detail in order to not unnecessarily obscure the present invention. Reference throughout this specification to "one embodiment" or "an embodiment" means that a particular feature, configuration, composition, or characteristic described in connection with the embodiment is included in at least one embodiment of the present invention. Thus, the appearances of the phrase "in one embodiment" or "an embodiment" in various places throughout this specification are not necessarily referring to the same embodiment of the present invention. Additionally, the particular features, configurations, compositions, or characteristics may be combined in any suitable manner in one or more embodiments.

Unless otherwise stated in the specification, all the scientific and technical terms used in the specification have the same meanings as commonly understood by those skilled in the technical field to which the present invention.

In one embodiment of the present invention, the term "probiotics" refers to bacteria that exert beneficial effects on the intestinal environment when reached the intestines after intake. Most probiotics known to date are lactic acid bacteria, and include some *Bacillus* species and the like. Since Elie Metchnikoff (a Russian scientist) received a Nobel prize for his discovery that the reason why Bulgarians enjoy longevity is because of the intake of milk fermented with *Lactobacillus*, the functionalities of lactic acid bacteria and probiotics have been studied for a long time. In order for bacteria including lactic acid bacteria to be recognized as probiotics, these bacteria should resist gastric acid and bile acid, reach the small intestines, proliferate and colonize in the intestines, exhibit useful effects in the intestinal tracts, and should be nontoxic and nonpathogenic.

About 1 kg of bacteria live in the human intestines, and the amount of bacteria present in the human intestines is substantially equal to the amount of food present in the human intestines, and bacteria account for about 40% of feces contents (excluding water) that are excreted every day.

When human feces are observed with a microscope, it can be seen that the feces consist mostly of bacterial clusters, and about 99% of these bacteria are anaerobic bacteria. In the case of healthy babies who eat mother's milk, 90% or more of feces bacteria are Bifidobacteria, and with age, Bifidobacteria gradually decrease, and intestinal harmful bacteria increases (Bifido Microfl 7:35-43, 1998). In this normal aging process, probiotics function to help maintain the distribution of intestinal flora at a healthy state.

In one embodiment of the present invention, the term "lactic acid bacteria" is also called "Lactobacilli" and refers to bacteria that ferment sugars to obtain energy and produce a large amount of lactic acid. The name "lactic acid bacteria" is a common name and does not indicate a taxonomic position. Those falling within the definition of lactic acid bacteria include genera such as *Lactobacillus, Lactococcus, Leuconostoc, Pediococcus, Bifidobacterium* and the like. These lactic acid bacteria are morphologically divided into cocci (*Lactococcus, Pediococcus*, and *Leuconostoc*) and bacilli (*Lactobacillus* and *Bifidobacterium*), and are gram-positive stained. These lactic acid bacteria grow well in a hypoxic environment and produce lactic acid from various sugars. These lactic acid bacteria mostly show acid resistance, and have very complex auxotrophy to require many kinds of amino acids or vitamins in addition to sugars, and some of these lactic acid bacteria cannot grow if micronutrients are not added thereto. Lactic acid bacteria are widely distributed in nature, including agricultural products, foods, and human or animal bodies, and the exact place of growth of any of these lactic acid bacteria cannot be seen. *Lactococcus* grows at 10° C., but does not grow at 45° C., has an optimal growth temperature of about 30° C., and shows normal fermentation. Many *Lactococcus* strains are used as starters for milk products in food processing. *Pediococcus* shows normal fermentation and is arranged in packets of four cells. It is classified, according to growth temperature, the optical rotation of lactic acid, etc., into 8 species. *Pediococcus* together with *Leuconostoc* is a major genus related to fermentation, and is less connected with living animal bodies. *Leuconostoc* shows abnormal fermentation, and is classified, according to sugar decomposition, growth, growth pH, etc., into 4 species. *Lactobacillus* is largely divided into two, one that shows normal fermentation, and the other that shows abnormal fermentation. It is classified, according to growth temperature, sugar decomposition, growth, the optical rotation of lactic acid produced, etc., into 55 species and 11 subspecies. *Lactobacillus* is a typical genus of lactic acid bacteria, is used for various fermented foods. It is a flora present in intestinal tracts, and has an importance relationship with human or animal health. *Bifidobacterium* is an obligately anaerobic, gram-positive *bacillus* showing abnormal fermentation, and mainly produces lactic acid and acetic acid as final products.

In one embodiment of the present invention, "P8 protein (protein No. 8)" refers to an 8 KDa protein fragment extracted from lactic acid bacteria (*Lactobacillus rhamnosus*) according to the production method described in an example of the present invention. The P8 protein of the present invention may be defined by a nucleotide sequence represented by SEQ ID NO: 1 or an amino acid sequence represented by SEQ ID NO: 2, and exhibits beneficial effects on the treatment of colorectal diseases.

In one embodiment of the present invention, "vector" refers to a small-sized DNA having self-replication ability, which is used in order to introduce and express a gene in a host in a recombinant DNA experiment. As the vector, a plasmid or a bacteriophage is usually used. The vector should satisfy the following conditions: it should be efficiently inserted into cells, should have a site that can be cleaved with a restriction enzyme so that it can be inserted in combination with other DNA, should have drug resistance so that it can be selected, and should have a marker gene.

In the present invention, "vector" means P8 protein or one comprising a DNA encoding the active site of P8 protein, but is not limited thereto.

In one embodiment of the present invention, "transformation" means that a DNA chain fragment or plasmid having a gene different from that of an original cell penetrates between the cells and binds to a DNA present in the original cell, thereby changing the genetic character of the cell. Transformation is often observed in bacteria, and may also be achieved by artificial genetic engineering. A cell or individual whose genetic character was changed by the transformation is referred to as a "transformant". Specifically, a cell transformed by receiving a DNA that is not its own DNA is referred to as a transformed competent cell. The transformed competent cell may be provided with a new genetic character through conjugation and transduction. Where the new character of bacteria transformed by means of virus such as bacteriophage is transferred to other bacteria, the transfer is referred to as transduction or transfection. Transduction differs from transformation in that virus is involved therein.

In the present invention, "transformant" means a cell or individual whose genetic character was changed by insertion of a vector comprising the P8 protein or a DNA encoding the active site of the P8 protein, and the cells whose genetic character was changed are preferably lactic acid bacteria cells, but are not limited thereto.

In one embodiment of the present invention, the term "colorectal diseases" refers to various diseases that occur in the large intestine, including, but not limited to, colorectal cancer, colonic polyps, colitis, ischemic bowel disease, dysentery, intestinal vascular dysplasia, diverticulosis, irritable bowel syndrome, Crohn's disease, and the like.

In one embodiment of the present invention, the term "pharmaceutical composition" means a composition that is administered for a specific purpose. For the purpose of the present invention, the pharmaceutical composition of the present invention may be at least one protein selected from the group consisting of amino acid sequences represented by SEQ ID NOs: 2 to 10, or may be a composition comprising, as an active ingredient, at least one protein selected from the group consisting of amino acid sequences represented by SEQ ID NOs: 2 to 10, and may comprise a protein and a pharmaceutically acceptable carrier, excipient or diluent, which are involved therein. The "pharmaceutically acceptable" carrier or excipient means one approved by a regulatory agency of the Federal or a state government, or one listed in the governmental pharmacopoeia or other generally recognized pharmacopoeia for use in vertebral animals, and more particularly in humans.

For parenteral administration, the pharmaceutical composition of the present invention can be in the form of suspensions, solutions, or emulsions, in oily or aqueous vehicles, and can be in the form of solid or semi-solid, preferably liquid. Furthermore, the pharmaceutical composition of the present invention can contain formulatory agents such as suspending, stabilizing, solubilizing, and/or dispersing agents, and can be sterilized. The pharmaceutical composition can be stable under the conditions of manufacture and storage and can be preserved against the contaminating action of microorganisms such as bacteria and fungi. Alternatively, the pharmaceutical composition of the present invention can be in sterile powder form for reconstitution with a suitable vehicle before use. The pharmaceutical composition can be presented in unit dose form, in microneedle patches, in ampoules, or other unit-dose containers, or in multi-dose containers. Alternatively, the pharmaceutical composition can be stored in a freeze-dried (lyophilized) condition requiring only the addition of sterile liquid carrier, for example, water for injection immediately prior to use. Extemporaneous injection solutions and suspensions can be prepared from sterile powders, granules or tablets.

In some non-limiting embodiments, the pharmaceutical composition of the present invention may be formulated as liquid or contained as microspheres in liquids. In some non-limiting embodiments, excipients that are suitable for the pharmaceutical composition of the present invention may include preservatives, suspending agents, stabilizers, dyes, buffers, antibacterial agents, antifungal agents, and isotonic agents, for example, sugars or sodium chloride. As used herein, the term "stabilizer" refers to a compound optionally used in the pharmaceutical composition of the present invention in order to increase storage life. In non-limiting embodiments, additional stabilizers may be sugars, amino acids or polymers. In addition, the pharmaceutical composition of the present invention can comprise one or more pharmaceutically acceptable carriers. The carrier can be a solvent or dispersion medium. Non-limiting examples of pharmaceutically acceptable carriers include water, saline, ethanol, polyol (e.g., glycerol, propylene glycol and liquid polyethylene glycol), oils, and suitable mixtures thereof. Non-limiting examples of sterilization techniques that are applied to the pharmaceutical composition of the present invention include filtration through a bacterial-retaining filter, terminal sterilization, incorporation of sterilizing agents, irradiation, sterilizing gas irradiation, heating, vacuum drying, and freeze drying.

In one embodiment of the present invention, "administration" means introducing the composition of the present invention into a patient by any suitable method. The composition of the present invention may be administered by any general route, as long as it can reach a target tissue. Specifically, the composition of the present invention may be administered orally, intraperitoneally, intravenously, intramuscularly, subcutaneously, intradermally, intranasally, intrapulmonary, intrarectally, intracavitally or intrathecally. However, a protein comprising at least one selected from the consisting of amino acid sequences represented by SEQ ID NOs: 2 to 10, or a pharmaceutical composition comprising the protein as an active ingredient of the present invention, is most preferably administered orally as a powder, tablet, capsule or liquid formulation, but is not limited thereto.

A method for treating colorectal disease according to the present invention may comprise administering a pharmaceutically effective amount of the pharmaceutical composition. In the present invention, the effective amount can be determined depending on various factors, including the kind of disease, the severity of the disease, the kinds and contents of active ingredient and other ingredients in the composition, the kind of formulation, the patient's age, body weight, general health condition, sex and diet, the time of administration, the route of administration, the secretion rate of the composition, the period of treatment, and other drugs that are concurrently used.

In one embodiment, the present invention provides a protein comprising any one or more amino acid sequences selected from the group consisting of SEQ ID NOs: 8, 9 and 10. Preferably, the protein is a protein represented by SEQ ID NO: 2. Preferably, the protein is a protein derived from lactic acid bacterial origin. The lactic acid bacteria are any one or more selected from the group consisting of *Lactobacillus rhamnosus, Lactobacillus acidophilus, Lactobacillus paracasei, Lactobacillus plantarum, Pediococcus pentosaceus*, and *Lactobacillus brevis*. Preferably, the lactic acid bacteria are *Lactobacillus rhamnosus*.

In another embodiment, the present invention provides a pharmaceutical composition for prevention or treatment of colorectal disease, which contains, as an active ingredient, a protein comprising any one or more amino acid sequences selected from the group consisting of SEQ ID NOs: 8, 9 and 10. Preferably, the colorectal disease is any one or more selected from the group consisting of colorectal cancer, colorectal polyp, colitis, ischemic bowel disease, dysentery, intestinal vascular dysplasia, diverticulosis, irritable bowel syndrome, and Crohn's disease. Preferably, the colorectal disease is colorectal cancer.

In still another embodiment, the present invention provides a food composition for prevention or alleviation of colorectal disease, which contains, as an active ingredient, a protein comprising any one or more amino acid sequences selected from the group consisting of SEQ ID NOs: 8, 9 and 10. Preferably, the colorectal disease is any one or more selected from the group consisting of colorectal cancer, colorectal polyp, colitis, ischemic bowel disease, dysentery, intestinal vascular dysplasia, diverticulosis, irritable bowel syndrome, and Crohn's disease. Preferably, the colorectal disease is colorectal cancer.

In still another embodiment, the present invention provides a vector configured to express a protein comprising any one or more amino acid sequences selected from the group consisting of SEQ ID NOs: 8, 9 and 10.

In still another embodiment, the present invention provides a transformant (excluding a human being) comprising a vector configured to express a protein comprising any one or more amino acid sequences selected from the group consisting of SEQ ID NOs: 8, 9 and 10. Preferably, the transformant is lactic acid bacteria. Preferably, the lactic acid bacteria are *Pediococcus pentosaceus*.

In still another embodiment, the present invention provides a pharmaceutical composition for prevention or treatment of colorectal disease, which contains, as an active ingredient, a transformant (excluding a human being) comprising a vector configured to express a protein comprising any one or more amino acid sequences selected from the group consisting of SEQ ID NOs: 8, 9 and 10. Preferably, the transformant is lactic acid bacteria. Preferably, the lactic acid bacteria are *Pediococcus pentosaceus*. Preferably, the colorectal disease is any one or more selected from the group consisting of colorectal cancer, colorectal polyp, colitis, ischemic bowel disease, dysentery, intestinal vascular dysplasia, diverticulosis, irritable bowel syndrome, and Crohn's disease. Preferably, the colorectal disease is colorectal cancer.

In still another embodiment, the present invention provides a food composition for prevention or alleviation of colorectal disease, which contains, as an active ingredient, a transformant (excluding a human being) comprising a vector configured to express a protein comprising any one or more amino acid sequences selected from the group consisting of SEQ ID NOs: 8, 9 and 10. Preferably, the transformant is lactic acid bacteria. Preferably, the lactic acid bacteria are *Pediococcus pentosaceus*. Preferably, the colorectal disease is any one or more selected from the group consisting of colorectal cancer, colorectal polyp, colitis, ischemic bowel disease, dysentery, intestinal vascular dysplasia, diverticulosis, irritable bowel syndrome, and Crohn's disease. Preferably, the colorectal disease is colorectal cancer.

Hereinafter, each step of the present invention will be described in detail.

Advantageous Effects

Although it is known that lactic acid bacteria are used as therapeutic agents against colorectal diseases, including colorectal cancer, colitis, irritable bowel syndrome, Crohn's disease and the like, the development of technologies related to the identification of a protein as an active ingredient in lactic acid bacteria and the use thereof is still insufficient. The present invention relates to a protein derived from lactic acid bacteria and a method for producing the same. The lactic acid bacteria-derived protein of the present invention is a purified protein isolated from lactic acid bacteria (*Lactobacillus rhamnosus*) having an excellent therapeutic effect against colorectal cancer. It has been demonstrated to have a remarkable effect against colorectal diseases, and thus is expected to be widely used as a natural protein therapeutic agent against colorectal diseases in the medical field.

DETAILED DESCRIPTION

Colorectal cancer DLD-1 cells were cultured in a 6-well plate at a density of $1.5 \times 10^6$ cells/well, and a P8 protein of the present invention was added thereto at a concentration of 1 µg/ml or 10 µg/ml. Next, the cells were incubated for 24 to 48 hours, and then washed twice with phosphate buffered saline and treated with 1 ml of a LIVE/DEAD viability/cytotoxicity staining kit, followed by incubation for 20 to 40 minutes. By the staining, living cells were stained green, and dead cells were stained red. The cells were observed under a fluorescent microscope, and the degree of inhibition of viability thereof was analyzed. As a result, it was shown that when the colorectal cancer cells were treated with the P8 protein, the viability of the cells decreased compared to that of a negative control, and the viability of the colorectal cancer cells decreased as the concentration or time of treatment with the P8 protein increased.

MODE FOR INVENTION

Hereinafter, the present invention will be described in further detail. It will be obvious to those skilled in the art that these examples are for illustrative purposes only and are not intended to limit the scope of the present invention.

Example 1: Isolation and Purification of Protein from Lactic Acid Bacteria

Example 1-1: Purification of Protein from Lactic Acid Bacteria

The colorectal cancer line DLD-1 was treated with culture supernatants or cell lysates of various kinds of lactic acid bacteria, and the anticancer activities thereof were examined. Among them, a *Lactobacillus rhamnosus* (KCTC 12202BP) cell lysate showing the highest anticancer activity was selected.

Figure 1:
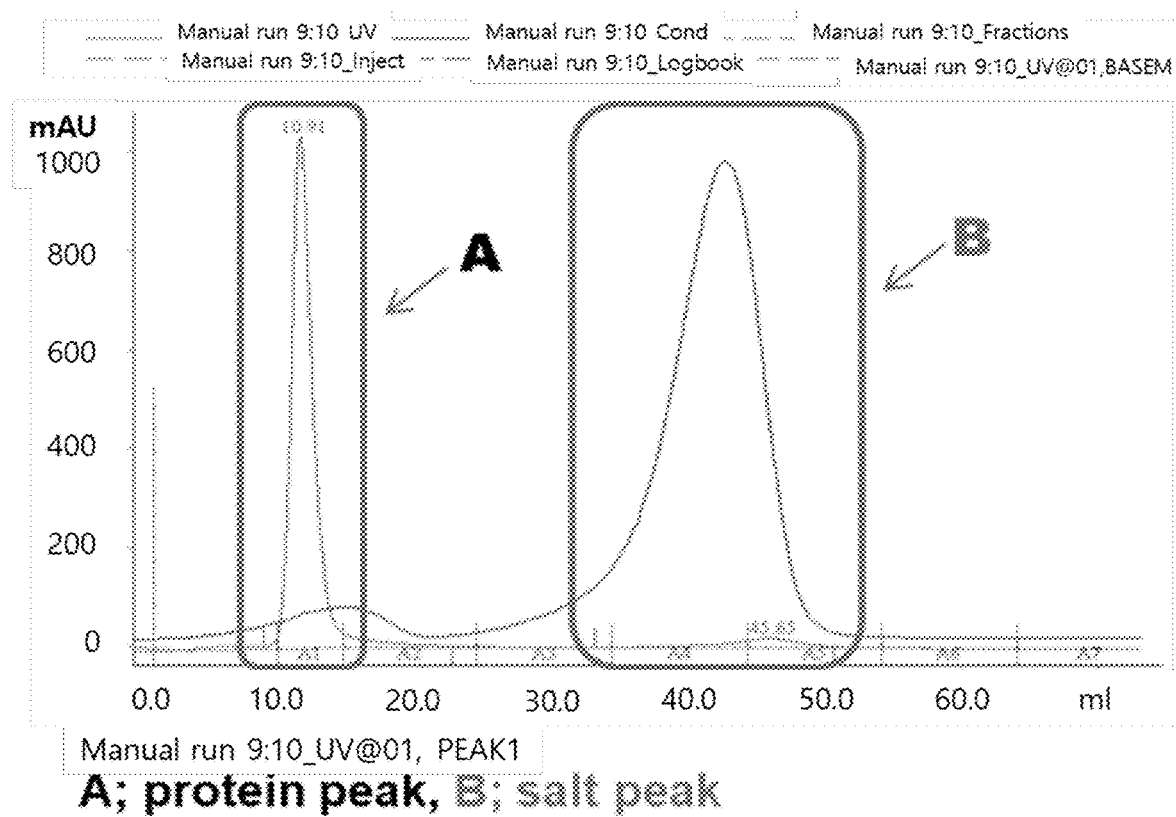
FIG. 1 shows the results of separating a *Lactobacillus rhamnosus* cell lysate by size exclusion chromatography into a protein and a low molecular material according to one example of the present invention.
Figure 2A:
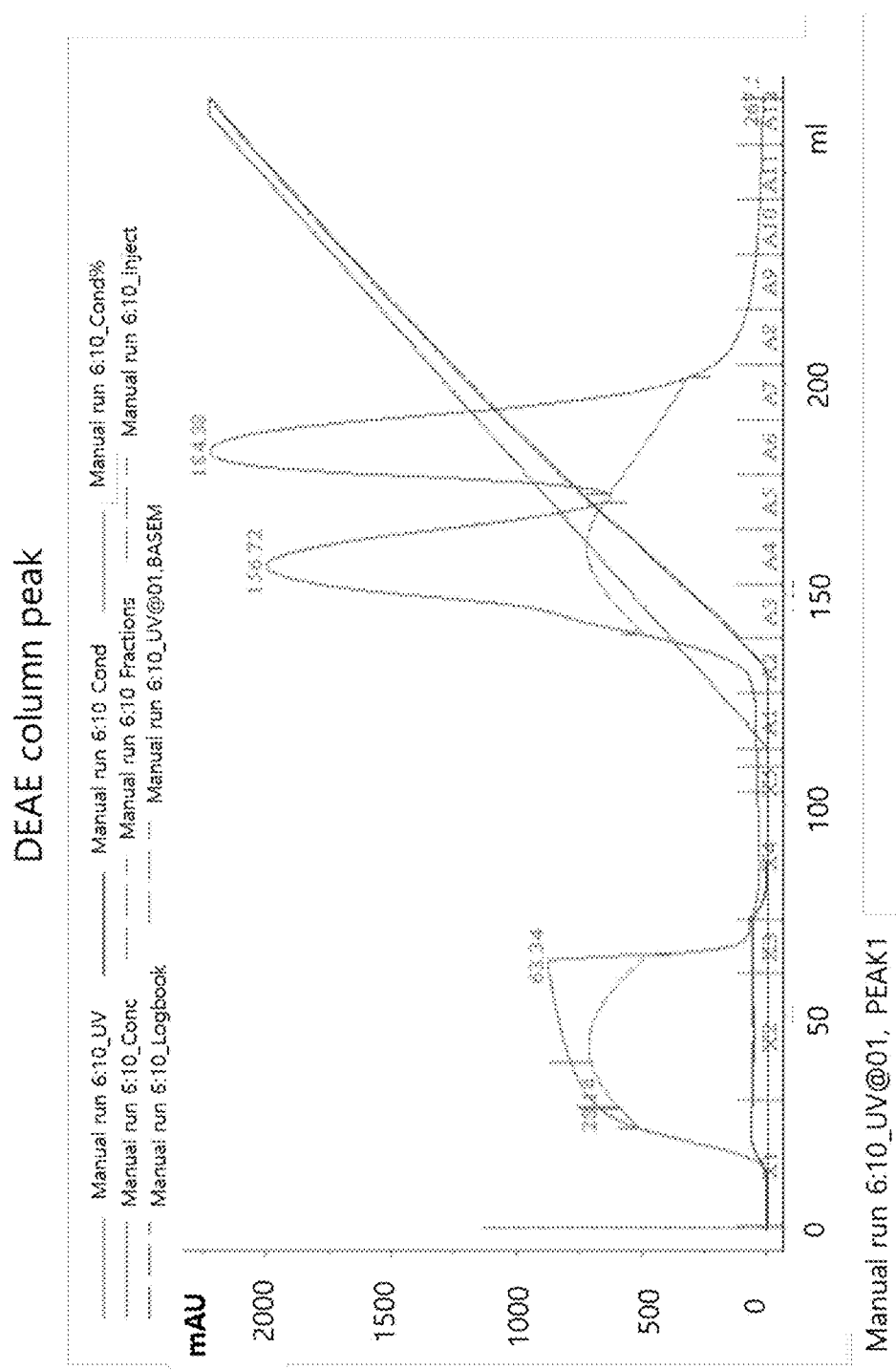
FIGS. 2A, 2B, 2C, and 2D show the results of each step of a protein purification process for producing a P8 protein of the present invention according to one example of the present invention.
Figure 2B:
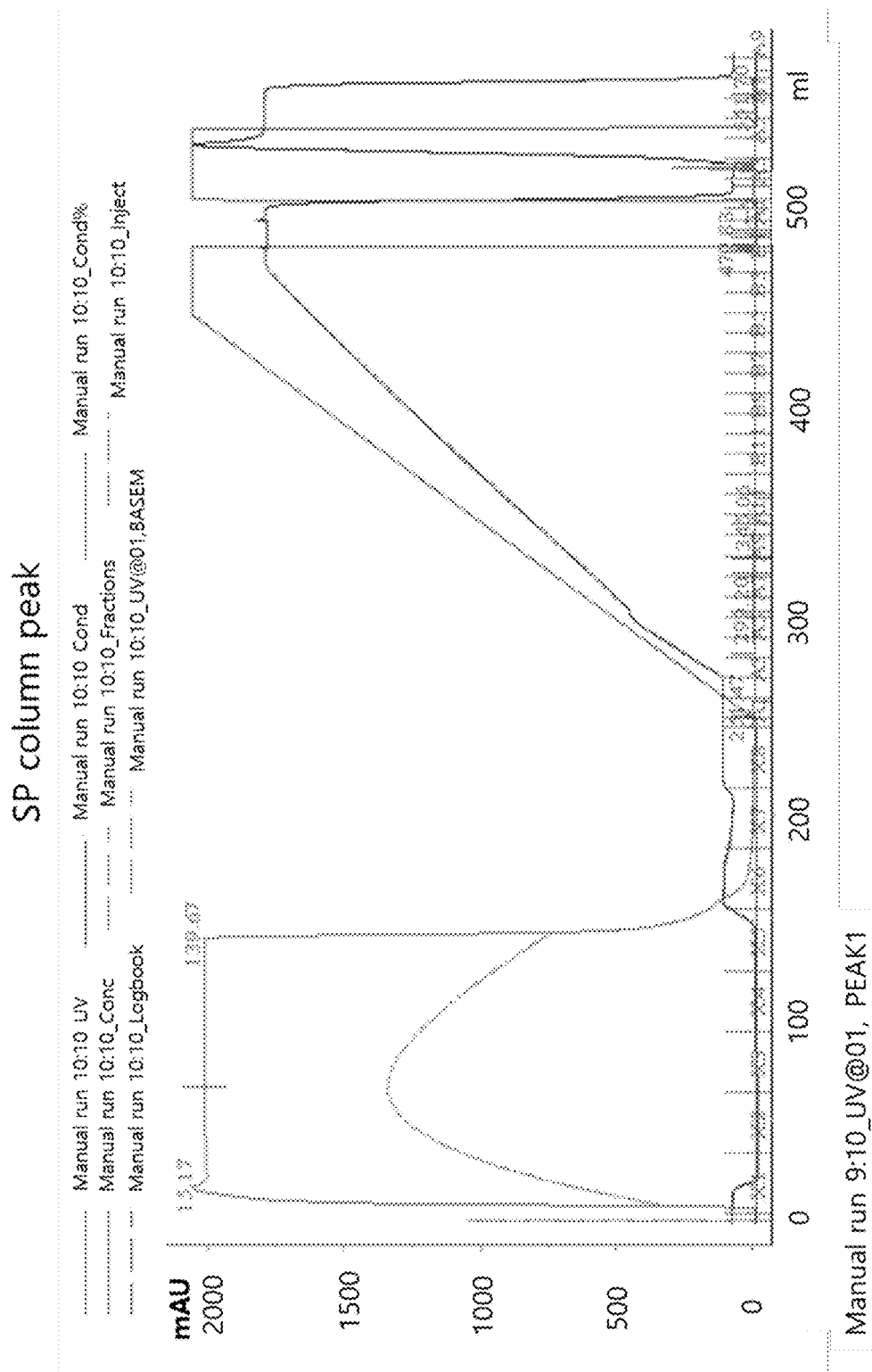
Figure 2C:
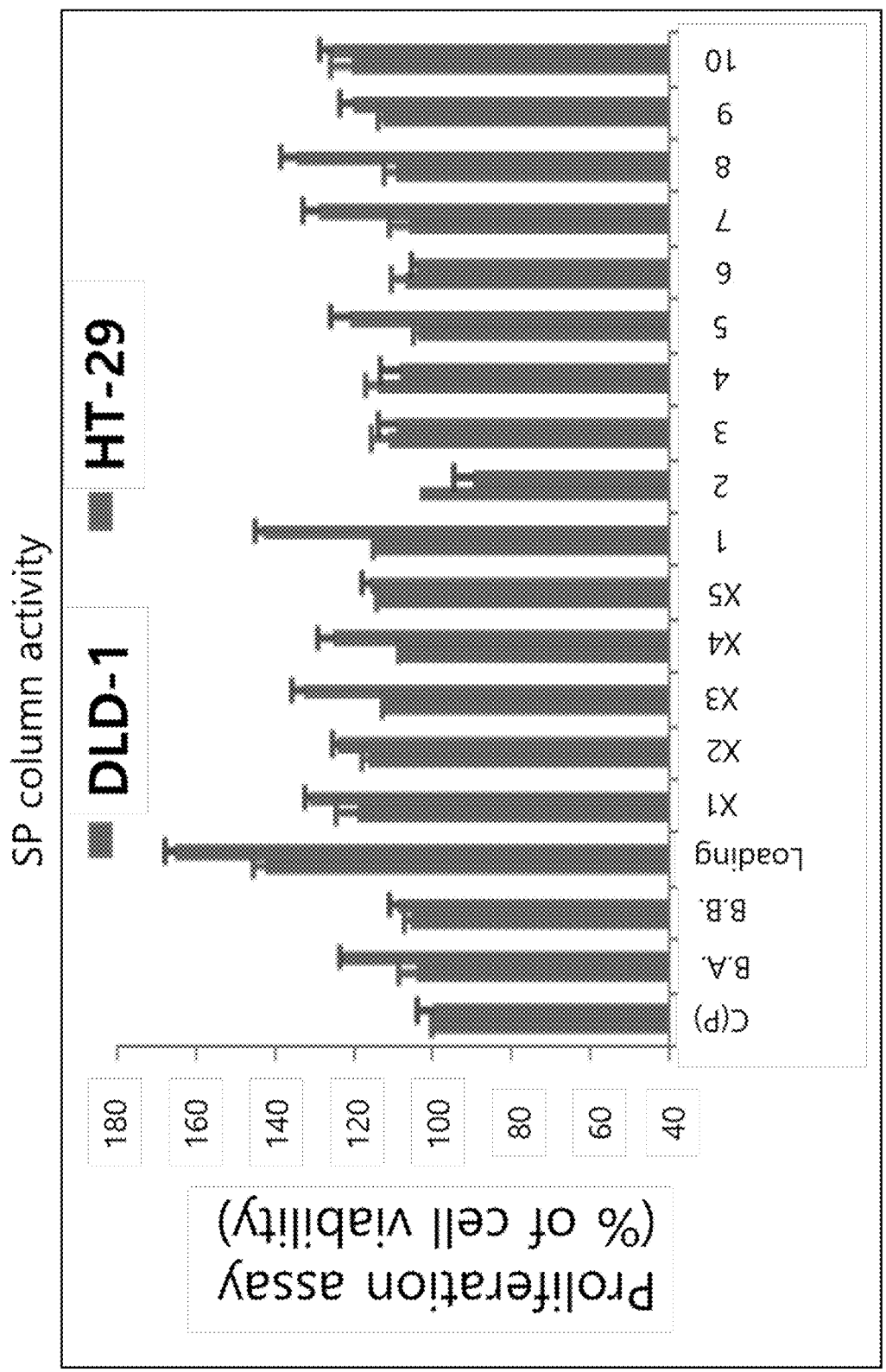
Figure 2D:
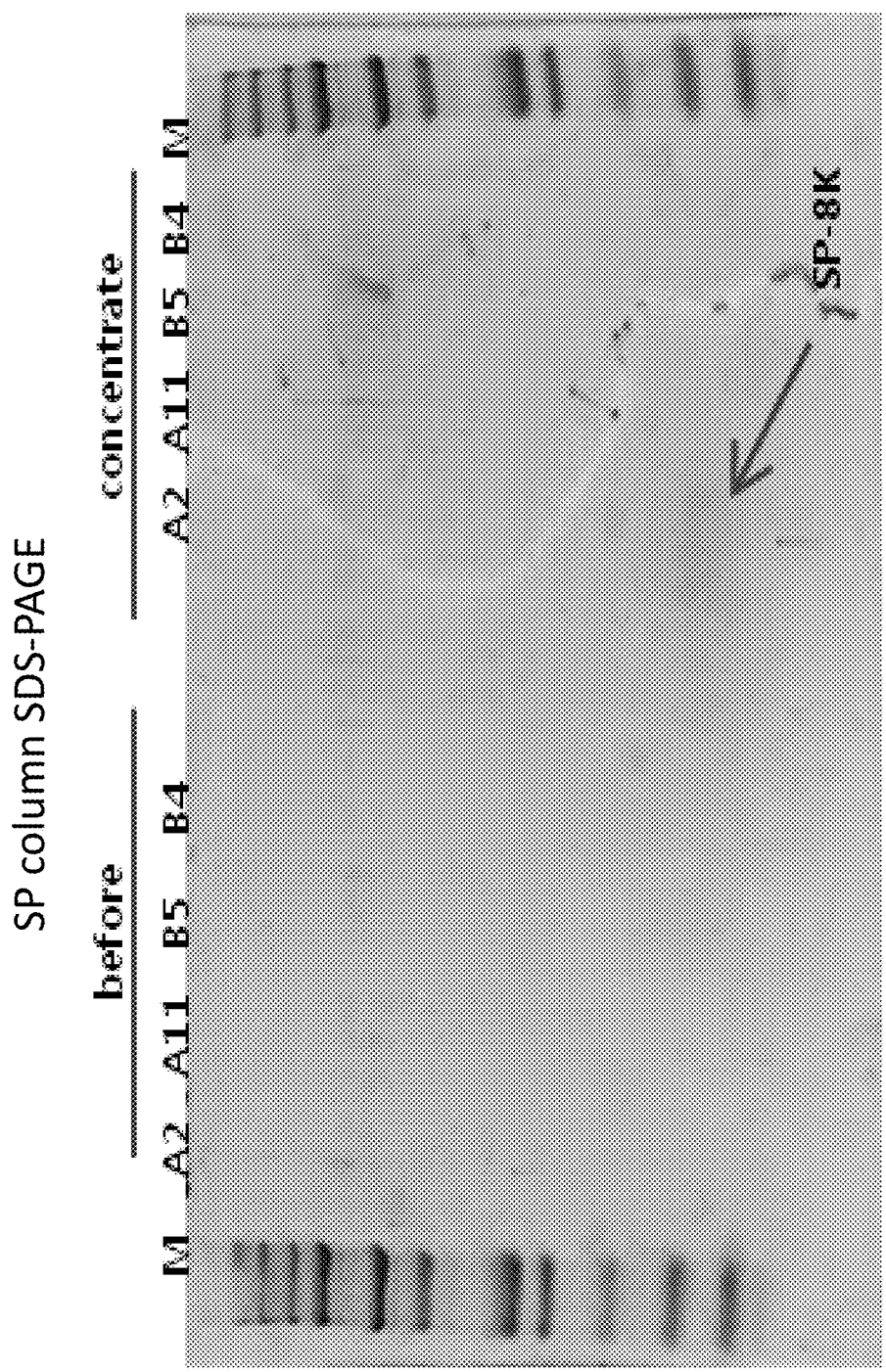

In order to purify an anticancer protein as an active ingredient from the *Lactobacillus rhamnosus* cell lysate, size exclusion chromatography (Sephadex G-25, desalting column, GE Healthcare) was performed using a FPLC (fast protein liquid chromatography) system (GE Healthcare), thereby isolating only the protein. A peak graph showing separation into the protein and a low molecular material is shown in FIG. 1.

The fraction containing only the separated protein was dialyzed against 20 mM Tris buffer (pH8.0), and the protein not adsorbed on HiTrap DEAE FF (GE Healthcare) was collected, concentrated through a 3-KDa membrane, and then dialyzed again against 0.05 M phosphate (pH 6.0) solution, adsorbed on HiTrap DEAE SP (GE Healthcare), and then subjected to sequential separation according to the concentration gradient of 0.5 M sodium chloride. Colorectal cancer cells were treated with each of the separated fractions, and the anticancer activities of the fractions were analyzed. The fraction having the highest anticancer activity was concentrated and analyzed by SDS-PAGE, thereby isolating an 8-KDa protein which was named "P8 protein". FIGS. 2A, 2B, 2C, and 2D show the results of each step of the process for producing the P8 protein.

Example 1-2: Purification of Protein Derived from Lactic Acid Bacteria

Figure 3:
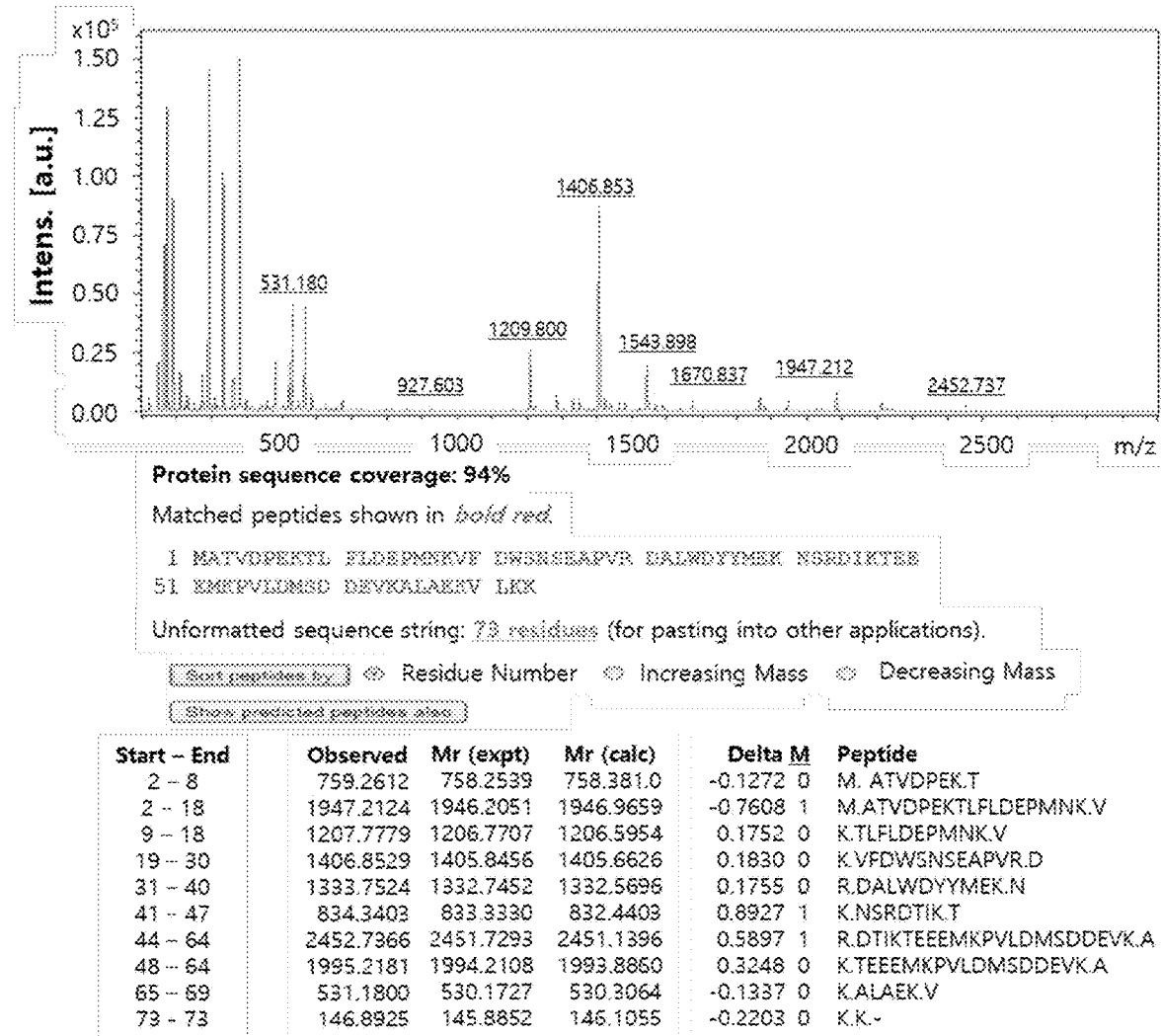
FIG. 3 shows the results of amino acid sequencing of a P8 protein of the present invention according to one example of the present invention.

The P8 protein purified by the method of Example 1-1 was stained with Coomassie Blue-250, and then subjected to MALDI-TOF (Matrix Assisted Laser Desorption Ionization Time Of Flight) mass spectrometry, thereby obtaining the ID "unidentified protein LGG_02452 [*Lactobacillus rhamnosus*]". The protein was transferred to a PVDF membrane and identified by N-terminal amino acid sequencing. As a result, it was found that the N-terminal amino acid sequence of the protein was A-T-V-D-P-E-K-T-L-F (SEQ ID NO: 11). The results are shown in FIG. 3.

In addition, using the DNA sequence of the "unidentified protein LGG_02452" as a template, PCR was performed with the primers shown in Table 1 below, and sequencing was performed. As a result, the nucleotide sequence and amino acid sequence of the protein were identified as shown in Table 2 below.

TABLE 1

Primer sequence of "unidentified protein LGG_02452"

| | | |
|---|---|---|
| Forward | (F) | 5'- atggaggtaatcattatggcaac-3' (SEQ ID NO: 12) |
| Reverse | (R) | 5'- cttcttgagaacctttctg-3' (SEQ ID NO: 13) |

TABLE 2

| Kind of sequence | SEQ ID NO | Sequence of "P8 protein" |
|---|---|---|
| Nucleotide sequence | SEQ ID NO: 1 | gcaacagtagatcctgaaaagacattgtt tctcgatgaaccaatgaacaaggtatttg actggagcaacagcgaagcacctgtacgt gatgcgctgtgggattattacatggaaaa gaacagccgtgataccatcaagactgaag aagaaatgaaaccagtcctagacatgtcc gacgatgaggtcaaagccctagcagaaaa aggttctcaagaagta |
| Amino acid sequence | SEQ ID NO: 2 | ATVDPEKTLFLDEPMNKVFDWSNSEAPVR DALWDYYMEKNSRDTIKTEEEMKPVLDMS DDEVKALAEKVLKK |

Figure 4:
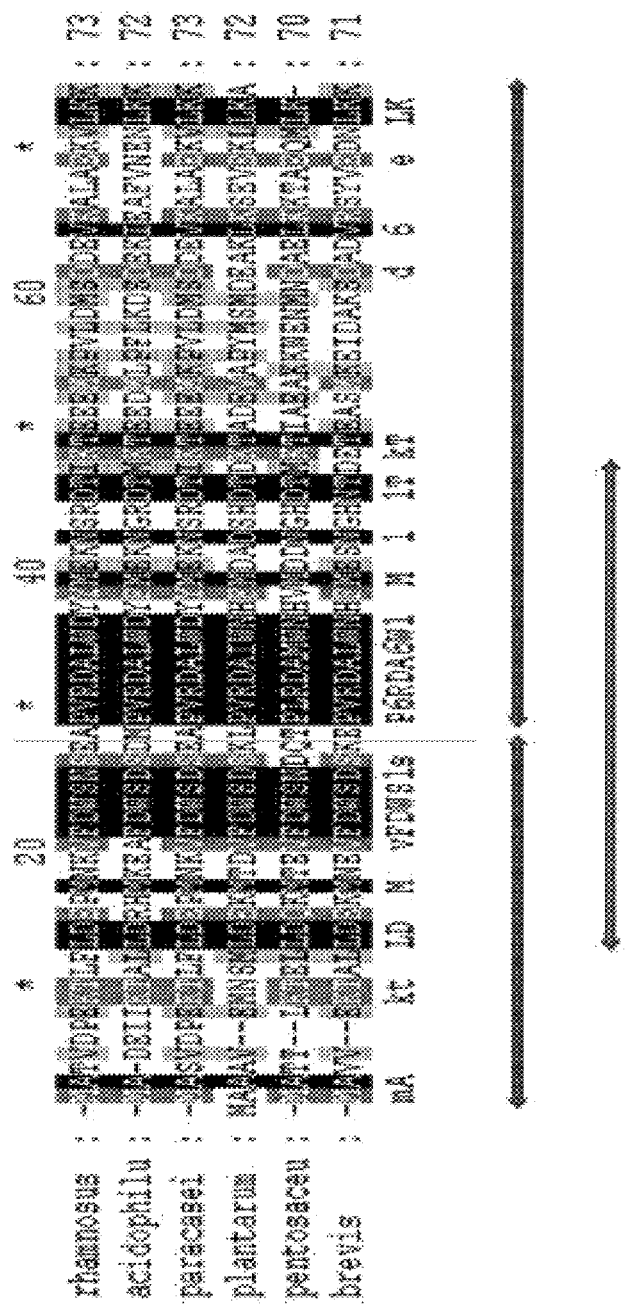
FIG. 4 is a schematic view showing active site sequences shared between lactic acid bacteria-derived proteins having high amino acid sequence homology with a P8 protein of the present invention, according to one example of the present invention.

Example 1-3: Identification of Active Site of Protein Derived from Lactic Acid Bacteria In order to trace the active site of the P8 protein purified in Example 1-1, lactic acid bacteria-derived proteins having sequences similar to that of the P8 protein were investigated, and the results are shown in Table 3 below. The sequences of three active sites determined by analyzing the sequence homology between the P8 protein and the proteins shown in Table 3 are shown in Table 4 below. FIG. 4 is a schematic view showing active site sequences shared between the lactic acid bacteria-derived proteins.

TABLE 3

| Lactic acid bacteria species | SEQ ID NO | Sequences of "P8 protein" and similar proteins derived from lactic acid bacteria |
|---|---|---|
| Lactobacillus rhamnosus | SEQ ID NO: 2 | ATVDPEKTLFLDEPMNKVFD WSNSEAPVRDALWDYYMEKNSRDTI KTEEEMKPVLDMSDDEVKALAEKVL KK |
| Lactobacillus acidophilus | SEQ ID NO: 3 | ADEIIKTALLDRHMKEAFDWSDSDMP VRDALWDYFMEKNGRDTMKTEEDML PFLKDSDEKIEAFVNENLKK |

TABLE 3-continued

| Lactic acid bacteria species | SEQ ID NO | Sequences of "P8 protein" and similar proteins derived from lactic acid bacteria |
|---|---|---|
| Lactobacillus paracasei | SEQ ID NO: 4 | ASVDPEKTLFLDEPMNKVFDWSDSEA PVRDALWDYYMEKNSRDTIKTEEEM KPVLDMSDDEVKALAEKVLKK |
| Lactobacillus plantarum | SEQ ID NO: 5 | AAAVEMNSMLDEKMTDVFDWSDSK LPVRDAIWNHFMDADSHDTDKTADE VAPYMSMDEAKLKSEVEKLLKA |
| Pediococcus pentosaceus | SEQ ID NO: 6 | ATTLKTELLDQKMTEVFDWSNDQTPL RDAMWNHVMDDNGHDTMKTIAEAK KWENMNDAELKKTAEQMLK |
| Lactobacillus brevis | SEQ ID NO: 7 | AVVEKTALLDEKMNEVFDWSDSKEP VRDALWNHFMESNGHNTDETEASMK EIDAKSDADVRSYVEDNLKK |

TABLE 4

| | Size | SEQ ID NO | Amino acid sequences of active sites |
|---|---|---|---|
| Active site 1 | 25 mer | SEQ ID NO: 8 | ATVDPEKTLFLDEPMNKVFDWSNSE |
| Active site 2 | 33 mer | SEQ ID NO: 9 | MNKVFDWSNSEAPVRDALWDYYMEKN SRDTIKT |
| Active site 3 | 47 mer | SEQ ID NO: 10 | APVRDALWDYYMEKNSRDTIKTEEEMK PVLDMSDDEVKALAEKVLKK |

Example 1-4: Examination of Anticancer Effect of Active Site of Protein Derived from Lactic Acid Bacteria Colorectal cancer DLD-1 cells were cultured in a 96-well plate at a density of $1 \times 10^4$ cells/well, and each of active sites 1 to 3 (SEQ ID NOs: 8 to 10) of Example 1-3 was added thereto at a concentration of 10 μg/ml. As a negative control, 0.1% PBS buffer used in protein purification was used. The cells were incubated for 24 hours, and then each well was treated with 100 of a cell survival rate measurement kit (Dojindo Cell count kit WST-8) and incubated for 2 hours. The absorbance of each well at 450 nm was measured using a microplate reader (Amersham, Biorad, USA, Japan), and based on the measured values, cell survival rates were calculated. As a result, it was shown that the cell growth of the colorectal cancer cell line DLD-1 in the test groups treated with active sites 1 to 3 was significantly inhibited compared to that of the negative control.

Figure 5:
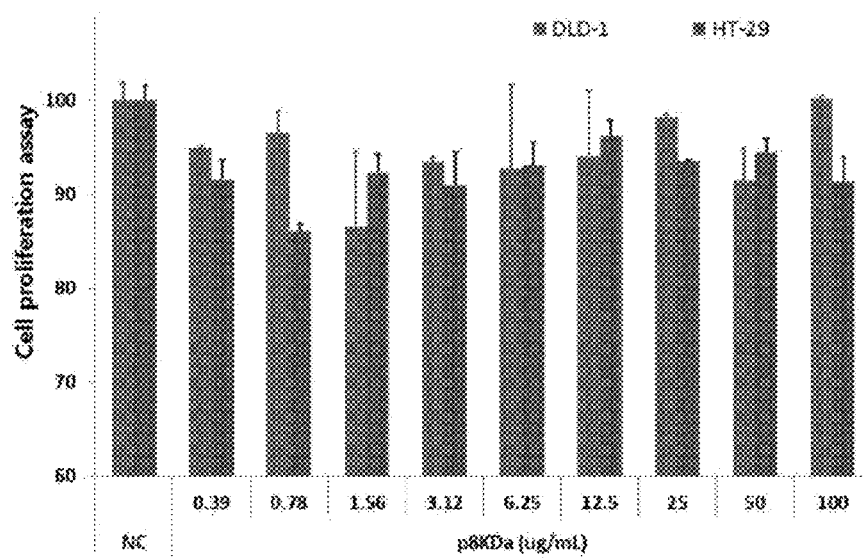
FIG. 5 shows the results of examining the cell growth inhibitory effect of a P8 protein of the present invention after treating colorectal cancer cell lines (DLD-1 and HT-29) with the P8 protein according to one example of the present invention.

Example 2: In Vitro Evaluation of Anticancer Effect of Protein (P8 Protein) Derived from Lactic Acid Bacteria Example 2-1: Analysis of Cell Survival Rate Each of the colorectal cancer cell line DLD-1 and the HT-29 cell line was cultured in a 96-well plate at a density of $1 \times 10^4$ cells/well, and the P8 protein of Example 1 was added thereto at a concentration of 0.39 μl/ml to 100 μl/ml. As a negative control, 0.1% PBS buffer used in protein purification was used. The cells were incubated for 24 hours, and then each well was treated with 100 of a cell survival rate measurement kit (Dojindo Cell count kit WST-8) and incubated for 2 hours. The absorbance of each well at 450 nm was measured using a microplate reader (Amersham, Biorad, USA, Japan), and based on the measured values, cell survival rates were calculated. The results are shown in FIG. 5.

As a result, it was shown that the P8 protein showed a cell growth inhibitory effect of about 20% against the colorectal cancer cell lines (DLD-1 and HT-29), indicating that it has an inhibitory effect on the growth of cancer cells.

Example 2-2: Evaluation of Anticancer Effect

Figure 6:
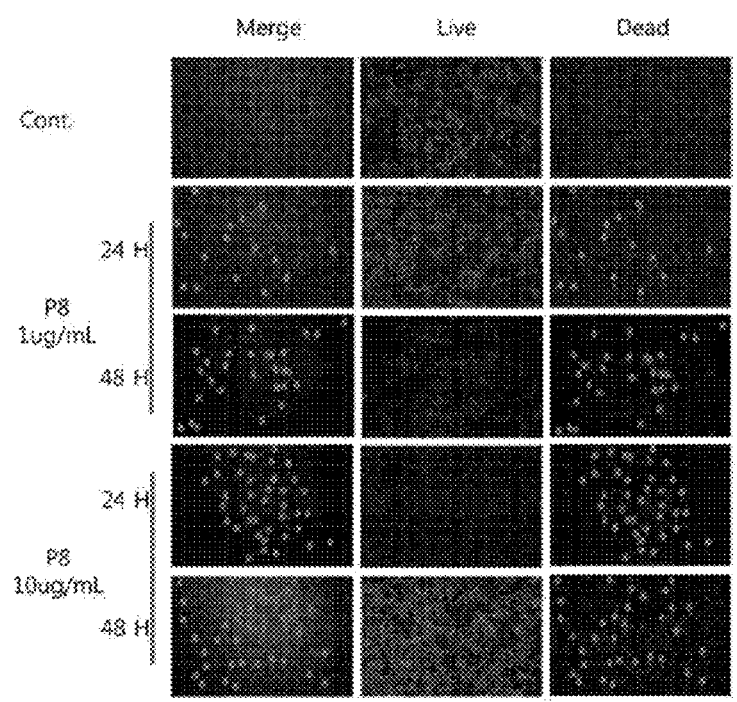
FIG. 6 shows the results of examining the cell viability inhibitory effect of a P8 protein of the present invention after treating a colorectal cancer cell line (DLD-1) with the P8 protein according to one example of the present invention.

Colorectal cancer DLD-1 cells were cultured in a 6-well plate at a density of $1.5 \times 10^6$ cells/well, and the P8 protein of Example 1 was added thereto at a concentration of 1 µg/ml or 10 µg/ml. Each well was incubated for 24 to 48 hours, and then washed twice with phosphate buffered saline and treated with 1 ml of a LIVE/DEAD viability/cytotoxicity staining kit, followed by incubation for 20 to 40 minutes. By the staining, live cells were stained green, and dead cells were stained red. The cells were observed under a fluorescent microscope, and the degree of inhibition of viability thereof was analyzed. The results of the analysis are shown in FIG. 6. As a result, it was shown that when the colorectal cancer cells were treated with the P8 protein, the viability of the cells decreased compared to that of the negative control, and the viability of the colorectal cancer cell lines decreased as the concentration or time of treatment with the P8 protein increased.

Example 2-3: Analysis of Cytotoxicity

In order to examine whether the P8 protein of Example 1 is cytotoxic, a cytotoxicity assay was performed using the P8 protein, highly expressed in NIH3T3 cells (mouse embryonic fibroblast cells), and BSA (bovine serum albumin) as a positive control.

Figure 7:
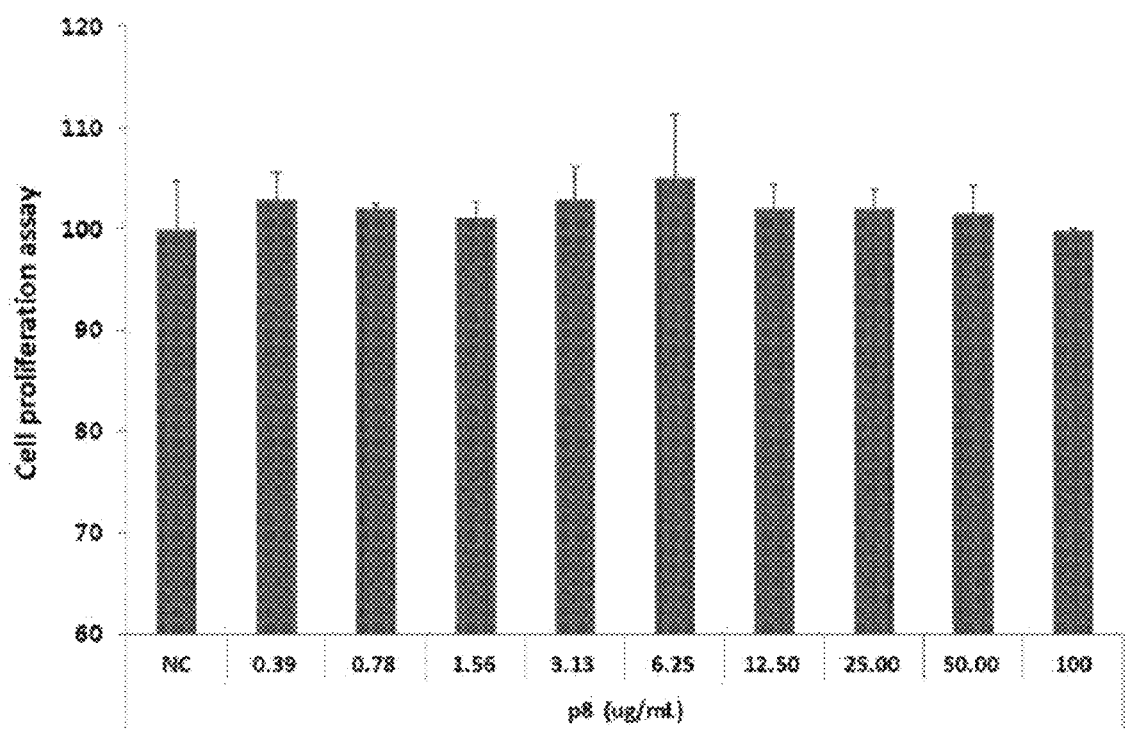
FIG. 7 shows the results of examining the cytotoxicity of a P8 protein of the present invention after treating NIH3T3 cells with the P8 protein according to one example of the present invention.

First, NIH3T3 cells were cultured in a 96-well plate at a density of $1 \times 10^4$ cells/well, and each of BSA and the highly expressed and purified P8 protein was added thereto at a concentration of 0.39 µg/ml to 100 µg/ml. Each well was incubated for 24 hours, and then treated with 100 of a cell survival rate measurement kit (Dojindo Cell count kit WST-8), followed by incubation for 2 hours. The absorbance of each well at 450 nm was measured using a microplate reader (Amersham, Biorad, USA, Japan), and based on the measured values, cell survival rates were calculated. The results are shown in FIG. 7.

As a result, it was shown that the survival rate of the cells treated with the P8 protein did not significantly differ from that of the cells treated with BSA, indicating that the P8 protein itself is not cytotoxic.

Example 2-4: Evaluation of Inhibitory Effect on Migration of Colorectal Cancer Cells Colorectal cancer DLD-1 cells were treated daily with 1 µg/ml of the P8 protein of Example 1 for 1, 3 or 7 days, and then dispensed into each well of a 6-well plate.

Figure 8:
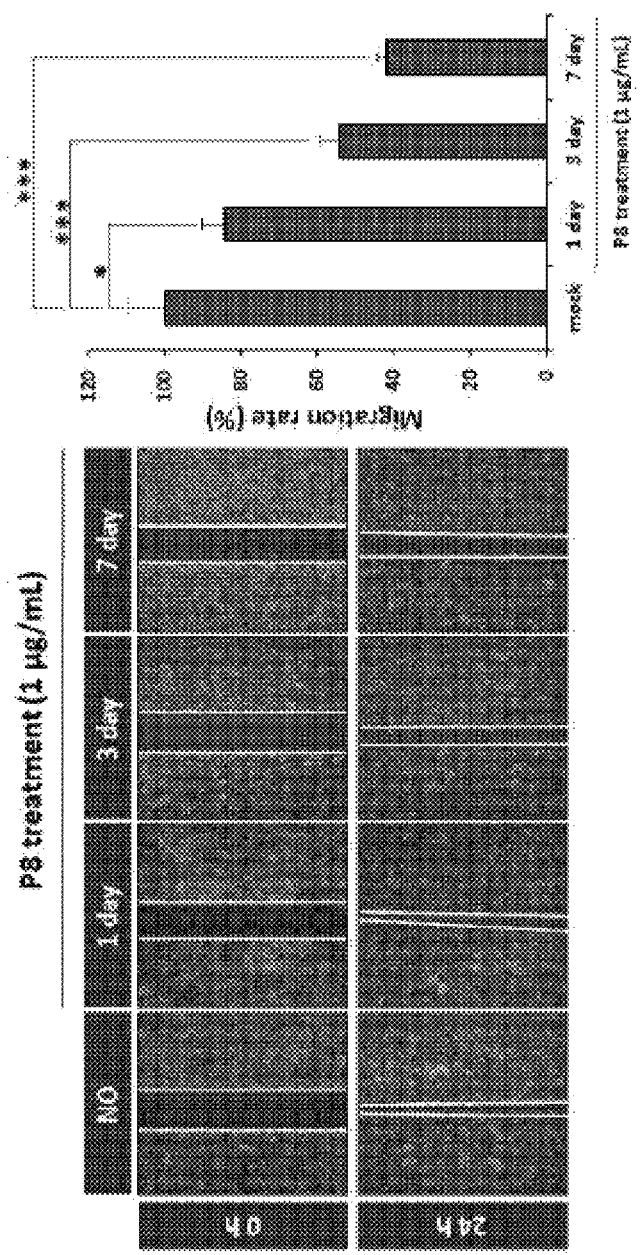
FIG. 8 shows the results of examining the cell migration inhibitory effect of a P8 protein of the present invention after treating a colorectal cancer cell line (DLD-1) with the P8 protein according to one example of the present invention.

The dispensed DLD-1 cells were cultured overnight, and then the plate having the cells cultured thereon was scratched with a 200 µl tip. To remove suspended material resulting from the scratch, the plate was washed twice with PBS, and then additionally incubated for 24 hours. The results are shown in FIG. 8.

As a result, it was shown that in the control group not treated with the P8 protein, the scratched portion was filled with the cells, whereas in the test group treated with the P8 protein, the rate at which the scratched portion was filled with the cells decreased. In particular, it was observed that the migration rate of the cells significantly decreased in proportion to the duration of time (1, 3 or 7 days) during which the cells were treated with the P8 protein. The results were statistically processed, and as a result, it was shown that the migration rate of the cells decreased by 15.7% for 1-day treatment with the P8 protein, 45.9% for 3-day treatment, and 58.3% for 7-day treatment, compared to the cell-filled area in the control group not treated with the P8 protein.

Example 3: In Vivo Evaluation of Anticancer Effect of Protein (P8 Protein) Derived from Lactic Acid Bacteria

Example 3-1: Construction of Colorectal Cancer Xenograft Models

The human colorectal cancer cell line (DLD-1) was transplanted subcutaneously into nude mice, thereby constructing xenograft models. Using the xenograft models, the anticancer activity of the P8 protein of Example 1 was evaluated.

First, for construction of colorectal cancer xenograft models, DLD-1 cells were transplanted subcutaneously into nude mice at a concentration of $1 \times 10^7$ cells/100 µl. 10 to 15 Days after the transplantation, the transplanted state of the tumor cells was checked, and mice showing a stable transplanted state were continuously observed. Before tumor's central necrosis occurred, mice showing rapid tumor growth due to supply of sufficient blood were selected, and tumor tissues were collected therefrom. Of the collected tumor tissue, the outer portion in which rapid cell division mainly occurred was cut into a predetermined size (3×3×3 mm), thereby constructing a tumor fragment. Then, the tumor fragment was placed on the tip of a puncture needle (Trocar), and the anterior side of the left rear leg of each animal was incised about 4 mm. The prepared puncture needle was inserted through the incision such that the tip reached the interbody side on the rear side of the left front leg. The puncture needle was removed by lightly and quickly turning it at an angle of 360° such that the tumor fragment was located at a target point. The incised portion was sterilized. The position of the tumor fragment was determined by touching the skin with hand. Tumor growth was observed twice or more a week, and only mice showing a successfully transplanted state were selected and used in an experiment.

Example 3-2: Evaluation of Anticancer Effect

The colorectal cancer xenograft models constructed according to the method of Example 3-1 were grouped as shown in Table 5 below, and were administered intraperitoneally with a drug twice a week for 4 weeks (a total of 8 times).

TABLE 5

| Group | | Drug administration |
|---|---|---|
| G1 | NC | PBS |
| G2 | PC1 | Anticancer agent: 5-fluorouracil_10 mg/Kg |
| G3 | PC2 | Anticancer agent: oxaliplatin_4 mg/Kg |
| G4 | T1 | P8 protein_1 mg/Kg |
| G5 | T2 | P8 protein_5 mg/Kg |
| G6 | T3 | P8 protein_10 mg/Kg |

Figure 9:
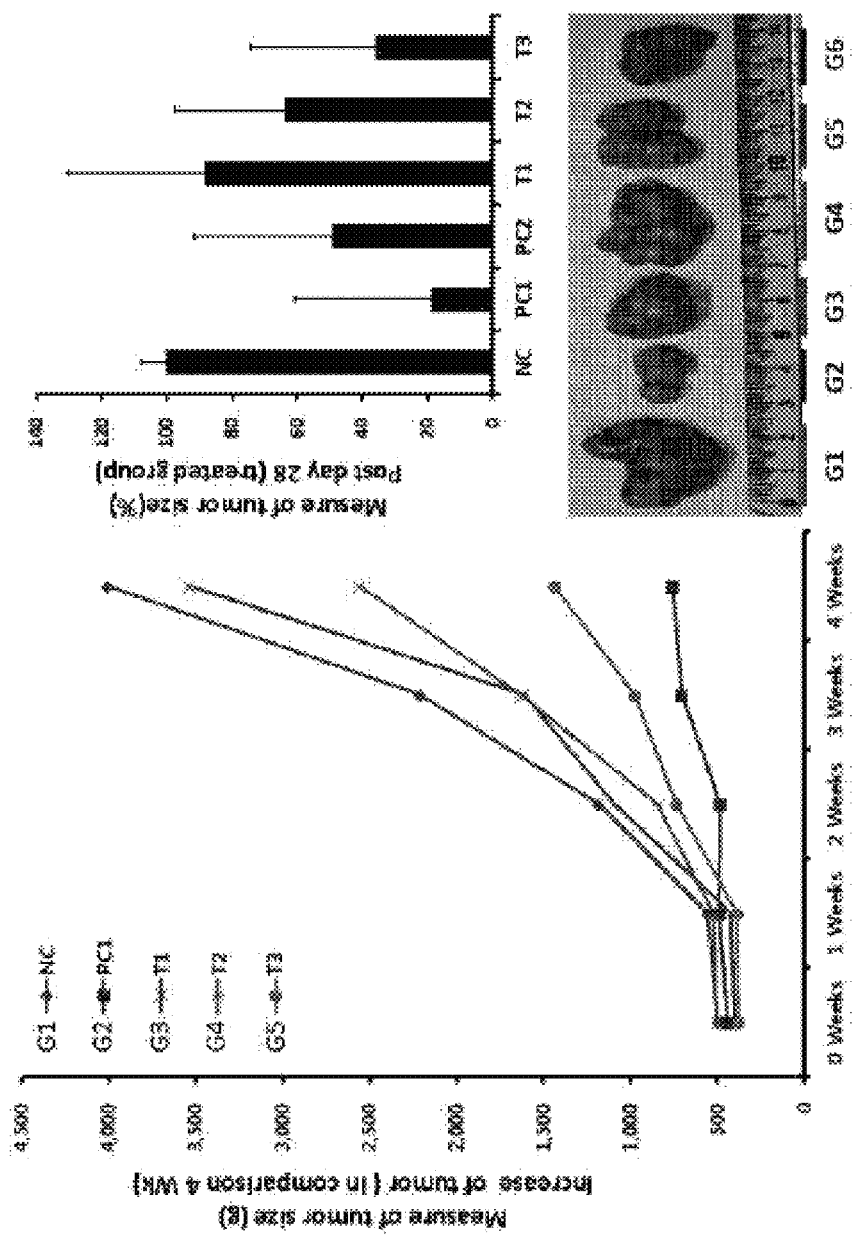
FIG. 9 shows the results of examining the cancer tissue growth inhibitory effect of a P8 protein of the present invention after treating colorectal cancer xenograft mouse models with the P8 protein according to one example of the present invention.

During drug administration, the tumor size was measured using Vernier calipers once every two days. Based on the measured value, the tumor volume was calculated using the equation shown in Table 6 below. After a total of 8-times administration, the tumors were dissected and photographed. FIG. 9 shows a graph obtained by calculating the volume and a photograph of the tumors dissected from the mice.

TABLE 6

| Tumor volume | {length of long axis × (length of short axis × length of short axis)}/2 |
|---|---|

As a result, it was shown that cancer growth in the test groups treated with all the concentrations of the P8 protein was significantly inhibited compared to that in the negative control group and that when the P8 protein was used for treatment at a concentration of 10 mg/Kg or higher, it could exhibit cancer growth inhibitory effects superior to those of conventional anticancer agents.

INDUSTRIAL APPLICABILITY

The present invention relates to a protein derived from lactic acid bacteria and a method for producing the same. The lactic acid bacteria-derived protein of the present invention is a purified protein isolated from lactic acid bacteria (*Lactobacillus rhamnosus*) having an excellent therapeutic effect against colorectal cancer. It has been demonstrated to have a remarkable effect against colorectal diseases, and thus is expected to be widely used as a natural protein therapeutic agent against colorectal diseases in the medical field.

```
                  Sequence List Text

SEQ ID NO: 1 (Lactobacillus rhamnosus, DNA)
gcaacagtag atcctgaaaa gacattgttt ctcgatgaac
caatgaacaa ggtatttgac tggagcaaca gcgaagcacc
tgtacgtgat gcgctgtggg attattacat ggaaaagaac
agccgtgata ccatcaagac tgaagaagaa atgaaaccag
tcctagacat gtccgacgat gaggtcaaag ccctagcaga
aaaggttctc aagaagtaa SEQ ID NO: 2 (Lactobacillus rhamnosus, PRT)
Ala Thr Val Asp Pro Glu Lys Thr Leu Phe Leu Asp
Glu Pro Met Asn Lys Val Phe Asp Trp Ser Asn Ser
Glu Ala Pro Val Arg Asp Ala Leu Trp Asp Tyr Tyr
Met Glu Lys Asn Ser Arg Asp Thr Ile Lys Thr Glu
Glu Glu Met Lys Pro Val Leu Asp Met Ser Asp Asp
Glu Val Lys Ala Leu Ala Glu Lys Val Leu Lys Lys SEQ ID NO: 3 (Lactobacillus acidophilus, PRT)
Ala Asp Glu Ile Ile Lys Thr Ala Leu Leu Asp Arg
His Met Lys Glu Ala Phe Asp Trp Ser Asp Ser Asp
Met Pro Val Arg Asp Ala Leu Trp Asp Tyr Phe Met
Glu Lys Asn Gly Glu Asp Met Leu Pro Phe Leu Arg
```

```
                  Sequence List Text

Asp Thr Met Lys Thr Glu Lys Asp Ser Asp Glu Lys
Ile Glu Ala Phe Val Asn Glu Asn Leu Lys Lys

SEQ ID NO: 4 (Lactobacillus paracasei, PRT)
Ala Ser Val Asp Pro Glu Lys Thr Leu Phe Leu Asp
Glu Pro Met Asn Lys Val Phe Asp Trp Ser Asp Ser
Glu Ala Pro Val Arg Asp Ala Leu Trp Asp Tyr Tyr
Met Glu Lys Asn Ser Arg Asp Thr Ile Lys Thr Glu
Glu Glu Met Lys Pro Val Leu Asp Met Ser Asp Asp
Glu Val Lys Ala Leu Ala Glu Lys Val Leu Lys Lys SEQ ID NO: 5 (Lactobacillus plantarum, PRT)
Ala Ala Ala Val Glu Met Asn Ser Met Leu Asp Glu
Lys Met Thr Asp Val Phe Asp Trp Ser Asp Ser Lys
Leu Pro Val Arg Asp Ala Ile Trp Asn His Phe Met
Asp Ala Asp Ser His Asp Thr Asp Lys Thr Ala Asp
Glu Val Ala Pro Tyr Met Ser Met Asp Glu Ala Lys
Leu Lys Ser Glu Val Glu Lys Leu Leu Lys Ala SEQ ID NO: 6 (Pediococcus pentosaceus, PRT)
Ala Thr Thr Leu Lys Thr Glu Leu Leu Asp Gln Lys
Met Thr Glu Val Phe Asp Trp Ser Asn Asp Gln Thr
Pro Leu Arg Asp Ala Met Trp Asn His Val Met Asp
Asp Asn Gly His Asp Thr Met Lys Thr Ile Ala Glu
Ala Lys Lys Trp Glu Asn Met Asn Asp Ala Glu Leu
Lys Lys Thr Ala Glu Gln Met Leu Lys SEQ ID NO: 7 (Lactobacillus brevis, PRT)
Ala Val Val Glu Lys Thr Ala Leu Leu Asp Glu Lys
Met Asn Glu Val Phe Asp Trp Ser Asp Ser Lys Glu
Pro Val Arg Asp Ala Leu Trp Asn His Phe Met Glu
Ser Asn Gly His Asn Thr Asp Glu Thr Glu Ala Ser
Met Lys Glu Ile Asp Ala Lys Ser Asp Ala Asp Val
Arg Ser Tyr Val Glu Asp Asn Leu Lys Lys SEQ ID NO: 8 (Lactobacillus rhamnosus, PRT)
Ala Thr Val Asp Pro Glu Lys Thr Leu Phe Leu Asp
Glu Pro Met Asn Lys Val Phe Asp Trp Ser Asn Ser
Glu SEQ ID NO: 9 (Lactobacillus rhamnosus, PRT)
Met Asn Lys Val Phe Asp Trp Ser Asn Ser Glu Ala
Pro Val Arg Asp Ala Leu Trp Asp Tyr Tyr Met Glu
Lys Asn Ser Arg Asp Thr Ile Lys Thr SEQ ID NO: 10 (Lactobacillus rhamnosus, PRT)
Ala Pro Val Arg Asp Ala Leu Trp Asp Tyr Tyr Met
Glu Lys Asn Ser Arg Asp Thr Ile Lys Thr Glu Glu
Glu Met Lys Pro Val Leu Met Ser Asp Asp Glu Val
Lys Ala Leu Ala Glu Lys Val Leu Lys Lys
```

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

This invention was made with Korean Government support under a grant No. S2367890 funded by the Ministry of Trade, Industry and Energy, under the supervision of the Republic of Korea Small and Medium Business Administration, from the WC300 project for developing drug-delivery probiotics for treatment of inveterate intestinal disease, study period was 2016 Feb. 1-2020 Dec. 31.

What is claimed is:

1. A method of treating or alleviating colorectal cancer comprising:
    administering to a person in need of such treatment a therapeutically effective amount of a composition comprising a peptide consisting of an amino acid sequence selected from the group consisting of SEQ ID NOs: 8, 9 and 10.

2. The method of claim 1, wherein the composition is in a form of a pharmaceutical composition.

3. The method of claim 1, wherein the composition is in a form of a food composition.

4. A method of treating or alleviating colorectal cancer comprising:
    administering to a person in need of such treatment a therapeutically effective amount of a composition comprising a transformant wherein the transformant is lactic acid bacteria comprising a vector constructed to express a peptide consisting of an amino acid sequence selected from the group consisting of SEQ ID NOs: 8, 9, and 10.

5. The method of claim 4, wherein the lactic acid bacteria are *Pediococcus pentosaceus*.

6. The method of claim 4, wherein the composition is in a form of a pharmaceutical composition.

7. The method of claim 4, wherein the composition is in a form of a food composition.

8. The method of claim 4, wherein the peptide is one derived from lactic acid bacteria of *Lactobacillus rhamnosus*.

* * * * *

SEQUENCE LISTING

<160> NUMBER OF SEQ ID NOS: 13

<210> SEQ ID NO 1
<211> LENGTH: 222
<212> TYPE: DNA
<213> ORGANISM: Lactobacillus rhamnosus

<400> SEQUENCE: 1

```
atggcaacag tagatcctga aaagacattg tttctcgatg aaccaatgaa caaggtattt      60
gactggagca acagcgaagc acctgtacgt gatgcgctgt gggattatta catggaaaag    120
aacagccgtg ataccatcaa gactgaagaa gaaatgaaac cagtcctaga catgtccgac    180
gatgaggtca agccctagc agaaaaggtt ctcaagaagt aa                        222
```

<210> SEQ ID NO 2
<211> LENGTH: 73
<212> TYPE: PRT
<213> ORGANISM: Lactobacillus rhamnosus

<400> SEQUENCE: 2

```
Met Ala Thr Val Asp Pro Glu Lys Thr Leu Phe Leu Asp Glu Pro Met
1               5                   10                  15
Asn Lys Val Phe Asp Trp Ser Asn Ser Glu Ala Pro Val Arg Asp Ala
                20                  25                  30
Leu Trp Asp Tyr Tyr Met Glu Lys Asn Ser Arg Asp Thr Ile Lys Thr
            35                  40                  45
Glu Glu Glu Met Lys Pro Val Leu Asp Met Ser Asp Asp Val Lys
        50                  55                  60
Ala Leu Ala Glu Lys Val Leu Lys Lys
65                  70
```

<210> SEQ ID NO 3
<211> LENGTH: 72
<212> TYPE: PRT
<213> ORGANISM: Lactobacillus acidophilus

<400> SEQUENCE: 3

```
Met Ala Asp Glu Ile Ile Lys Thr Ala Leu Leu Asp Arg His Met Lys
1               5                   10                  15
Glu Ala Phe Asp Trp Ser Asp Ser Asp Met Pro Val Arg Asp Ala Leu
                20                  25                  30
Trp Asp Tyr Phe Met Glu Lys Asn Gly Arg Asp Thr Met Lys Thr Glu
            35                  40                  45
Glu Asp Met Leu Pro Phe Leu Lys Asp Ser Asp Glu Lys Ile Glu Ala
        50                  55                  60
Phe Val Asn Glu Asn Leu Lys Lys
65                  70
```

<210> SEQ ID NO 4
<211> LENGTH: 73
<212> TYPE: PRT
<213> ORGANISM: Lactobacillus paracasei

<400> SEQUENCE: 4

```
Met Ala Ser Val Asp Pro Glu Lys Thr Leu Phe Leu Asp Glu Pro Met
1               5                   10                  15
Asn Lys Val Phe Asp Trp Ser Asp Ser Glu Ala Pro Val Arg Asp Ala
                20                  25                  30
Leu Trp Asp Tyr Tyr Met Glu Lys Asn Ser Arg Asp Thr Ile Lys Thr
            35                  40                  45
Glu Glu Glu Met Lys Pro Val Leu Asp Met Ser Asp Asp Val Lys
        50                  55                  60
Ala Leu Ala Glu Lys Val Leu Lys Lys
65                  70
```

<210> SEQ ID NO 5
<211> LENGTH: 72
<212> TYPE: PRT
<213> ORGANISM: Lactobacillus plantarum

<400> SEQUENCE: 5

Met Ala Ala Val Glu Met Asn Ser Met Leu Asp Glu Lys Met Thr
1               5                   10                  15

Asp Val Phe Asp Trp Ser Asp Ser Lys Leu Pro Val Arg Asp Ala Ile
            20                  25                  30

Trp Asn His Phe Met Asp Ala Asp Ser His Asp Thr Asp Lys Thr Ala
            35                  40                  45

Asp Glu Val Ala Pro Tyr Met Ser Met Asp Glu Ala Lys Leu Lys Ser
    50                  55                  60

Glu Val Glu Lys Leu Leu Lys Ala
65                  70

<210> SEQ ID NO 6
<211> LENGTH: 70
<212> TYPE: PRT
<213> ORGANISM: Pediococcus pentosaceus

<400> SEQUENCE: 6

Met Ala Thr Thr Leu Lys Thr Glu Leu Leu Asp Gln Lys Met Thr Glu
1               5                   10                  15

Val Phe Asp Trp Ser Asn Asp Gln Thr Pro Leu Arg Asp Ala Met Trp
            20                  25                  30

Asn His Val Met Asp Asp Asn Gly His Asp Thr Met Lys Thr Ile Ala
            35                  40                  45

Glu Ala Lys Lys Trp Gly Asn Met Asn Asp Ala Glu Leu Lys Lys Thr
    50                  55                  60

Ala Glu Gln Met Leu Lys
65                  70

<210> SEQ ID NO 7
<211> LENGTH: 71
<212> TYPE: PRT
<213> ORGANISM: Lactobacillus brevis

<400> SEQUENCE: 7

Met Ala Val Val Glu Lys Thr Ala Leu Leu Asp Glu Lys Met Asn Glu
1               5                   10                  15

Val Phe Asp Trp Ser Asp Ser Lys Glu Pro Val Arg Asp Ala Leu Trp
            20                  25                  30

Asn His Phe Met Glu Ser Asn Gly His Asn Thr Asp Glu Thr Glu Ala
            35                  40                  45

Ser Met Lys Glu Ile Asp Ala Lys Ser Asp Ala Asp Val Arg Ser Tyr
    50                  55                  60

Val Glu Asp Asn Leu Lys Lys
65                  70

<210> SEQ ID NO 8
<211> LENGTH: 25
<212> TYPE: PRT
<213> ORGANISM: Lactobacillus rhamnosus

<400> SEQUENCE: 8

Ala Thr Val Asp Pro Glu Lys Thr Leu Phe Leu Asp Glu Pro Met Asn
1               5                   10                  15

```
Lys Val Phe Asp Trp Ser Asn Ser Glu
            20                  25
```

<210> SEQ ID NO 9
<211> LENGTH: 33
<212> TYPE: PRT
<213> ORGANISM: Lactobacillus rhamnosus

<400> SEQUENCE: 9

```
Met Asn Lys Val Phe Asp Trp Ser Asn Ser Glu Ala Pro Val Arg Asp
1               5                   10                  15

Ala Leu Trp Asp Tyr Tyr Met Glu Lys Asn Ser Arg Asp Thr Ile Lys
            20                  25                  30

Thr
```

<210> SEQ ID NO 10
<211> LENGTH: 47
<212> TYPE: PRT
<213> ORGANISM: Lactobacillus rhamnosus

<400> SEQUENCE: 10

```
Ala Pro Val Arg Asp Ala Leu Trp Asp Tyr Tyr Met Glu Lys Asn Ser
1               5                   10                  15

Arg Asp Thr Ile Lys Thr Glu Glu Glu Met Lys Pro Val Leu Asp Met
            20                  25                  30

Ser Asp Asp Glu Val Lys Ala Leu Ala Glu Lys Val Leu Lys Lys
        35                  40                  45
```

<210> SEQ ID NO 11
<211> LENGTH: 10
<212> TYPE: PRT
<213> ORGANISM: Artificial Sequence
<220> FEATURE:
<223> OTHER INFORMATION: LGG_02452 [Lactobacillus rhamnosus]

<400> SEQUENCE: 11

```
Ala Thr Val Asp Pro Glu Lys Thr Leu Phe
1               5                   10
```

<210> SEQ ID NO 12
<211> LENGTH: 23
<212> TYPE: DNA
<213> ORGANISM: Artificial Sequence
<220> FEATURE:
<223> OTHER INFORMATION: LG_02452 forward primer

<400> SEQUENCE: 12
atggaggtaa tcattatggc aac                                         23

<210> SEQ ID NO 13
<211> LENGTH: 20
<212> TYPE: DNA
<213> ORGANISM: Artificial Sequence
<220> FEATURE:
<223> OTHER INFORMATION: LGG_02452 reverse primer

<400> SEQUENCE: 13
cttcttgaga accttttctg                                             20